United States Patent [19]

Kishi et al.

[11] 4,281,059
[45] Jul. 28, 1981

[54] PHOTOGRAPHIC MATERIAL

[75] Inventors: Kenichi Kishi; Takashi Sasaki, both of Hino, Japan

[73] Assignee: Konishiroku Photo Industry Co., Ltd., Tokyo, Japan

[21] Appl. No.: 100,234

[22] Filed: Dec. 4, 1979

[30] Foreign Application Priority Data

Dec. 12, 1978 [JP] Japan .................. 53-154402

[51] Int. Cl.³ .................................... G03C 1/34
[52] U.S. Cl. .................................. 430/551; 430/614
[58] Field of Search ................... 430/614, 551, 600

[56] References Cited

U.S. PATENT DOCUMENTS

| | | | |
|---|---|---|---|
| 3,804,633 | 4/1974 | Sakamoto et al. | 430/614 |
| 3,808,005 | 4/1974 | Willems et al. | 430/614 |
| 3,843,372 | 10/1974 | Jefferson | 430/614 |

FOREIGN PATENT DOCUMENTS 741228 11/1955 United Kingdom .

Primary Examiner—J. Travis Brown
Attorney, Agent, or Firm—Bierman & Bierman

[57] ABSTRACT

A photographic material comprising a support and at least one silver halide emulsion layer coated thereon, which material comprises a compound represented by the following general formula [I]:

General formula [I]

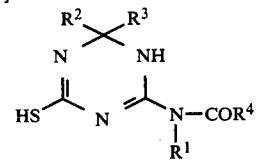

wherein $R^1$ represents a hydrogen atom or a substituted or unsubstituted aryl group, $R^2$ and $R^3$ individually represents a hydrogen atom, an alkyl group, alkenyl group, a substituted or unsubstituted aryl group, or $R^2$ and $R^3$ represent nonmetal atoms necessary for forming by their mutual linkage a 5- or 6-membered ring, and $R^4$ represents a hydrogen atom, an alkyl group, alkenyl group, a substituted or unsubstituted aryl group or a group of the general formula

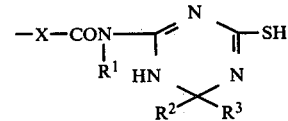

wherein X represents the group $-(CH_2)_n-$ wherein n is an integer from 0 to 4, or an allylene group.

7 Claims, No Drawings

PHOTOGRAPHIC MATERIAL

This application claims the priority of Japanese application No. 154,402/1978, filed Dec. 12, 1978.

This invention relates to silver halide photographic materials and particularly to stable silver halide photographic materials which are less suffering from fog formation.

Silver halide photographic materials generally have such a tendence that the higher becomes the sensitivity of the photographic material, the more becomes pronounced the fog formation. In addition thereto, the so-called high temperature development is often applied to a variety of silver halide photographic materials in order to shorten the developing time as aforesaid, said process being carried out at a temperature above 30° C. In this process, however generally the higher is the development temperature, the more becomes pronounced the fog formation. Furthermore, this fog formation tendency becomes more remarkable as coating speed or drying speed is increased at the time of preparing silver halide photographic materials for the purpose of increasing productivity.

Various means have heretofore been proposed to reduce such formation of fog as may be seen in light-sensitive silver halide photographic materials. It is known as most typical of such means to incorporate an antifoggant into silver halide emulsion layers or layers adjacent thereto, the working mechanism of which is detailed on page 396 et seq. of T. H. James, "The Theory of Photographic Process," Macmillan. Antifoggants hitherto used for the above purpose include azole compounds having nitro or mercapto groups, such as 4-nitro-5-methylbenzotriazole, 2-mercaptobenzoimidazole, 5-mercapto-1-phenyltetrazole, etc. Some of these compounds are not sufficient in their fog inhibiting effect when they are used in small amounts and, when they are used in such large amounts that the fog inhibition effect can be sufficiently obtained, there is brought about a decrease in sensitivity, though the fog is sufficiently effected thereby. On the other hand, others have the fog inhibition effect, but they are high in desensitization effect because of their being strongly absorbed by photosensitive nuclei in silver halide emulsions. In order to improve such drawbacks of these compounds as mentioned above, the so-called inhibitor precursor technique wherein an antifoggant such as the above-mentioned 5-mercapto-1-phenyltetrazole or the like is released during processing into a developer has been proposed as disclosed, for example, in Japanese Patent Publication No. 12077/1972. In the process according to this technique, however, not only synthesis of the precursor compounds is difficult but also special solvents and a special method of incorporation of the compounds are needed, and consequently this process involves a great difficulty when it is adopted and carried out in an industrial scale. Other antifoggants heretofore known include such 4-alkyl-3-amino-5-mercapto-1,2,4-triazole and compound derived therefrom by acylation of the amino group as disclosed in British Patent Specification No. 741,228 or the like. These compounds, however, have a considerably strong desensitization effect, though they have a sufficient fog inhibiting effect. In addition thereto, these compounds, because of the use of isothiocyanates as the staring materials for the synthesis thereof, have much difficulty in the use thereof in an industrial scale even from the standpoint of odor and toxicity.

Accordingly, a primary object of the present invention is to provide stable light-sensitive silver halide photographic materials which are prevented from fog formation and also free from desensitization.

A sendond object of the present invention is to provide light-sensitive silver halide photographic materials less suffering from fog formation even when subjected to development at high temperature.

A third object of the present invention is to provide antifoggants having been improved in drawbacks associated with the prior art as aforesaid.

The above-mentioned objects of the present invention can be accomplished in silver halide photographic materials comprising at least one compound represented by the following general formula [I], General formula [I]

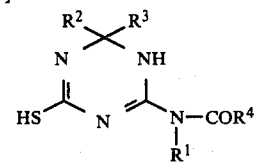

wherein $R^1$ represents a hydrogen atom or a substituted or unsubstituted aryl group wherein a hydrogen atom is preferable; $R^2$ and $R^3$ individually represents a hydrogen atom, an alkyl group, alkenyl group, a substituted or unsubstituted aryl group, or $R^2$ and $R^3$ represent nonmetal atoms necessary for forming by their-mutual linkage a 5- or 6-membered ring; and $R_4$ represents a hydrogen atom, an alkyl group, alkenyl group, a substituted or unsubstituted aryl group or a group of the general formula

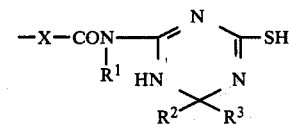

wherein X represents the group $-(CH_2)_n-$ (in which in represents a value of 0, 1, 2, 3, or 4) or an allylene group, and $R^1$, $R^2$ and $R^3$ are individually as defined above.

In the general formula [I], the aryl group represented by $R^1$, $R^2$, $R^3$ or $R^4$ includes substituted or unsubstituted phenyl and naphthyl whose substituents are individually halogen, lower alkyl, lower alkoxy, etc., i.e., p-chlorophenyl, o-methoxyphenyl, naphthyl, 4-chloronaphthyl, 4-methylnaphthyl, etc., the alkyl group represented by $R^2$, $R^3$ or $R^4$ may be either straight chain or branched alkyl having preferably 1 to 18 carbon atoms and includes, for example, methyl, ethyl, isopropyl, 2,2-dimethylpentyl, n-octyl and n-dodecyl, and similarly the alkenyl group may be either straight chain or branched alkenyl having preferably 3 to 18 carbon atoms and include, for example, allyl, butenyl, octenyl and oleyl. In case where $R^2$ and $R^3$ form a ring, examples of the ring are cyclopentyl and cyclohexyl which may be substituted by a methyl group. The allylene group represented by X includes o-phenylen, m-phenylene, p-phenylene, 1,4-naphthylene, 1,5-naphthylene, 5-methyl-1, 3-phenylene, etc.

Preferable embodiment of the compounds of the present invention has the following substituent in the general formula [I]:

$R_1$: a hydrogen atom.

$R_2$ and $R_3$: hydrogen atom or lower alkyl particularly methyl or ethyl.

$R_4$: lower alkyl, particularly methyl or ethyl.

The compounds represented by the aforesaid general formula [I] can be readily synthesized by acylating according to an ordinary procedure the compounds represented by the following general formula [II] or tautomers thereof.

General formula [II]

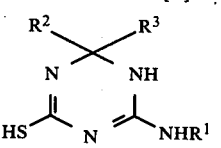

wherein $R^1$, $R^2$ and $R^3$ represent the same groups as represented by $R^1$, $R^2$ and $R^3$ respectively in the general formula [I].

The compounds represented by the aforesaid general formula [II] may be readily synthesized according to the procedure disclosed in "Chemical and Pharmaceutical Bulletin (Tokyo)," Vol. 26, 314–317 (1978).

Shown below for illustration but not for limitation are typical of the compound represented by the general formula [II].

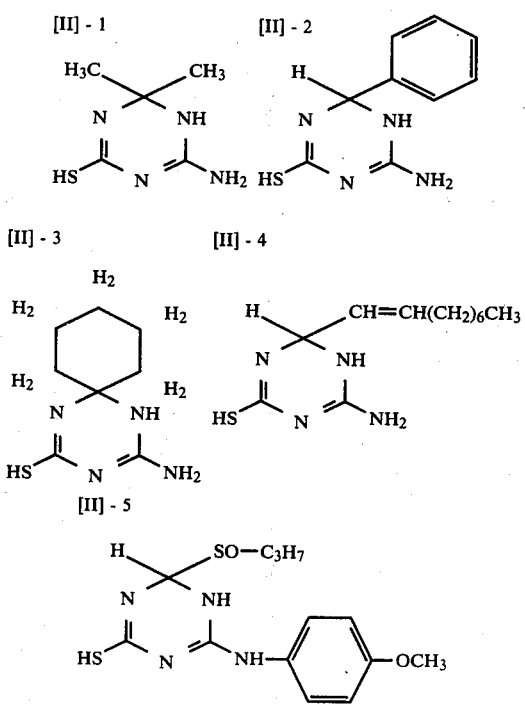

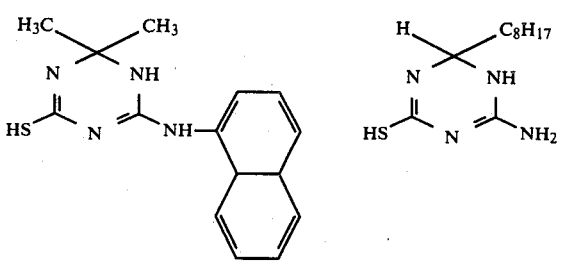

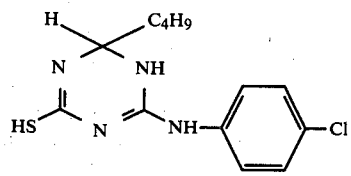

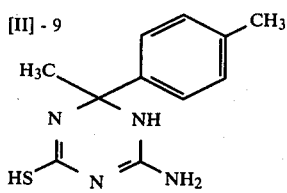

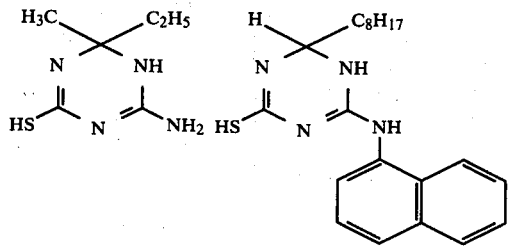

The compounds of the general formula [II] used for the synthesis of the compounds of the general formula [I] are illustrated below with reference to synthesis example.

SYNTHESIS EXAMPLE 1

Preparation of 6-amino-2,2-dimethyl-4-mercapto-1,2-dihydro-1,3,5-triazine (Exemplified compound [II]-1)

In the 200 ml of acetone was refluxed for 3 hours 7.1 g (0.06 mole) of amidinothiourea in the presence of 6 ml of piperidine. After having been allowed to cool, the reaction mixture was filtered to collect 7.6 g (in 80% yield) of colorless powder as deposited. Recrystallization from alcohol gave 7.0 g (in 74% yield) of colorless branch-like crystals, m.p. 186.5°–187.5° C.

SYNTHESIS EXAMPLE 2

Preparation of 6-(p-methoxyphenyl)-2-isopropyl-4-mercapto-1,2-dihydro-1,1,5-triazine (Exemplified compound [II]-5)

In 40 ml of anhydrous ethanol were refluxed for 8 hours 1.12 g (0.005 mole) of N-(p-methoxyphenyl)-amidino-thiourea and 0.42 g (0.006 mole) of secbutylaldehyde. Thereafter, most of the ethanol was removed by distillation under reduced pressure. After having ice-cold the residue, deposited crystals were collected by filtration to obtain 0.99 g (in 71% yield) of pale yellow powder. Recrystallization from ethanol gave 0.89 g (in 64% yield) of colorless needls, m.p. 193.5°-194° C.

Other compounds represented by the general formula [II] can be obtained according to procedures similar to those illustrated above.

The compounds represented by the general formula [I] according to the present invention (hereinafter called "the present compounds") can be readily synthesized by subjecting the compounds represented by the general formula [II] to ordinary acylation reaction. That is, the compounds of the general formula [I] may be obtained by allowing the compounds of the general formula [II] to react with acid anhydrides or acid halides. More concretely, the synthesis of the present compounds can readily be performed by reacting the compounds of the general formula [II] with acid anhydrides or acid halides, such as acetic anhydride, propionic anhydride, lauroyl chloride, benzoyl chloride, dichloride adipate and dichloride terephthalate, in the absence or presence of a solvent, such as anhydrous acetone, anhydrous ether, anhydrous acetonitrile, anhydrous benzene, glacial acetic or pyridine, and in the absence or presence of a basic catalyst such as pyridine, triethylamine, quinoline or picoline. The synthesis of the present compounds, however, can also be accomplished according to the so-called Schotten-Baumann reaction when the acid halides to be used are such acid halides relatively stable to water as lauroyl chloride, myristoyl chloride, stearyl chloride and oleyl chloride.

Typical examples of the present compounds exemplified below are given for illustrative but not limitative purpose.

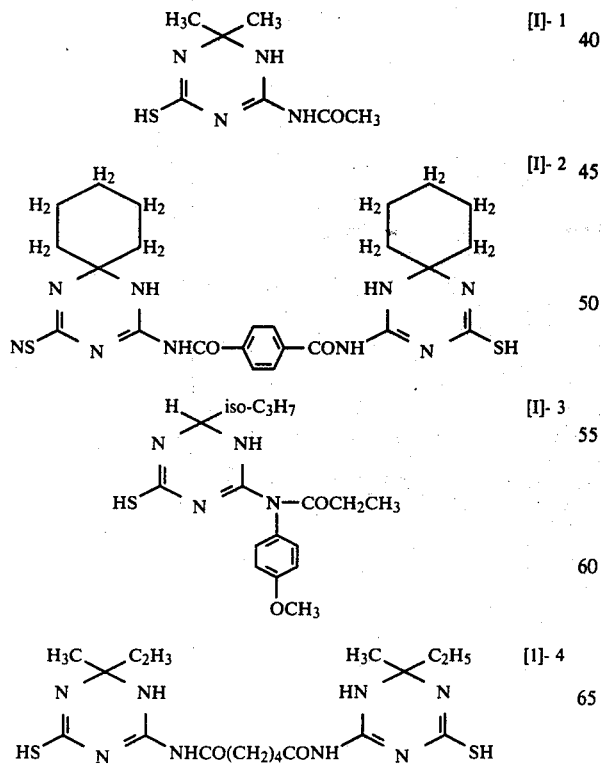

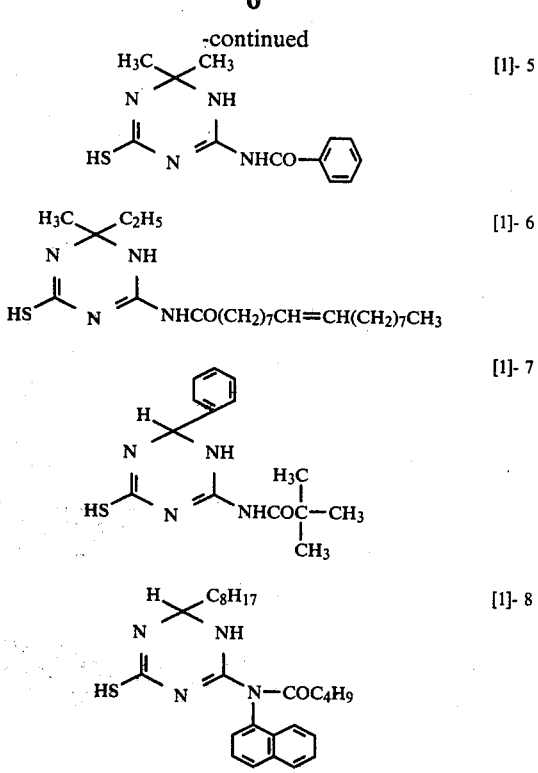

Given below are synthesis examples of the present compounds as exemplified above.

SYNTHESIS EXAMPLE 3

Preparation of 6-acetamido-2,2-dimethyl-4-mercapto-1,2-dihydro-1,3,5-triazine (Exemplified compound [I]-1)

In 4 ml of gracial acetic acid, 1.58 g (0.01 mole) of compound [II]-1 was allowed to react for 30 minutes under reflux with 4 ml of acetic anhydroide. After having allowed the reaction mixture to cool, pale yellow short needles desposited were collected by filtration to obtain 1.45 g (in 73% yield) of crude crystals. Recrystallization from water gave 1.26 g (in 63% yield) of colorless needle crystals, m.p. 205.5°-207° C.

SYNTHESIS EXAMPLE 4

Preparation of 6-benzamido-2,2-dimethyl-4-mercapto-1,2-dihydro-1,3,5-triazine (Exemplified compound [I]-5)

In 50 ml of acetonitrile were suspended 3.16 g (0.02 mole) of compound [II]-1 and 1.74 g (0.022 mole) of pyridine. To the suspension was added dropwise at room temperature 3.09 g (0.022 mole) of benzoyl chloride. After having been stirred at room temperature for 10 minutes, the mixture was allowed to undergo reaction under refluxed. After having allowed to cool, the reaction mixture was poured into about 500 ml of ice-cold water and a whitish yellow viscous substance separted was collected by decantation. The collected substance was washed with water-ethanol, the resulting washings were concentrated, and the residue was recrystallized from water-ethanol to obtain 1.78 g (in 34% yield) of colorless needle crystales, m.p. 176°-178° C.

In the same manner as above, there can be synthesized exemplified compound [I]-2 from compound [II]-3 and terephthaloyl chloride; exemplified compound [I]-3 from compound [II]-5 and propionyl chloride; exemplified compound [I]-4 from compound [II]-10 and adipoyl dhloride; exemplified compound [I]-6 from compound [II]-10 and oleoyl chloride; exemplified compound [I]-7 from compound [II]-1 and pivaroyl chloride; and exemplified compound [I]-8 from compound [II]-11 and valeryl chloride.

The present compounds other than those referred to above can also be synthesized in the same manner as explained above.

The present compounds are incorporated into silver halide emulsion (hereinafter called simply "the emulsion") layers and/or other layers adjacent thereto (e.g. intermediate layers such as protective layers, irradiation inhibiting layers and filter layers.). The present compounds, however, are preferably incorporated into the emulsion layers. Furthermore, the present compounds exhibit the fog ingibiting effect even when they are made present in a developer.

In incorporating the present compounds into the above-mentioned constituent layers of photographic materials, it is of advantage to add the present compound in the form of solution to the silver halide emulsion. Although a various solvents may be used for the above purpose, preferable is water or a water-miscible organic solvent which does not exert any adverse effect on the emulsion and other constituents of silver halide photographic materials. Preferred organic solvent include, for example, lower alcohols such as methanol, ethanol and isopropyl alcohol; ethylene glycol monoalkyl ethers such as ethylene glycol monomethyl ether, and ethylene glycol monoethyl ether; acid amides such as dimethylformamide, and dimethylacetamide; and others such as acetonitrile, tetrahydrofuran, dioxane and fluorinated alcohols; and these solvents may be used either singly or in admixtures thereof. However, when some of the present compounds are insoluble or very slightly soluble in the above-mentioned solvents such as water or water-miscible organic solvents, such compounds may be added to the silver halide emulsion after dispersing said compounds in water-immiscible solvents, such as tributyl phosphate, trioctyl phosphate and ethylene glycol monophenyl ether, so as to have the form of dispersion. Fundamentally, the present compounds may be added at any stage of the preparation of the photographic material. When it is added to the silver halide emulsion, preferably at the stage after the second repening, though the time during which the present compounds are incorporated into the emulsion may vary according to the kind of the resulting silver halide photographic material and the purpose for which the photographic material is used.

The amount of the present compounds to be incorporated may vary according to the kind, particle diameter and crystal pecularity of silver halide used in light-sensitive silver halide photographic materials, and to the presence of other photographic additives such as stabilizers, sensitizing dyes, etc., or depending on the temperature or the composition of processing liquid as which or with which the resulting light-sensitive silver halide photographic materials are processed. Generally, however, the amount of the present compounds used is 0.5 to 5000 mg, preferably 5 to 500 mg, per mole of silver halide.

Silver halide used in the present invention may be prepared according to a well known method, that is mixing in the presence of a solution of such high molecular substance as gelatin a solution of water-soluble halide (e.g. potassium bromide) with a solution of water-soluble silver salt (e.g. silver nitrate). The present invention is applicable to silver halide emulsions prepared by generally accepted procedures as disclosed in T. H. James, "The Theory of The Photographic Process," Macmillan and the like publications.

Light-sensitive silver halide photographic materials to which the present invention is applicable include color printing paper, color negative films, color positive films, black-and-white films (e.g. light-sensitive lithophotographic materials, light-sensitive X-ray photographic materials, etc.) and light-sensitive photographic materials for the diffusion transfer process.

The present compounds exhibit favorable for inhibiting effect even when they are incorporated either singly or plurally, and in the latter case they may be used either separately or simultaneously.

The present compounds may be allowed to simultaneously exist in silver halide photographic materials with other compounds which are incorporated therein with the view of preventing fog formation or fall in sensitivity that may occur during production step, starage and processing step of said photographic materials. Examples of such compounds as referred to above include known nitrogen containing heterocyclic compounds such as 4-hydroxy-6-methyl-1,3,3a,7-tetrazaindene, 5-mercapto-1-phenyltetrazole and 2-mercaptobenzothiazole, and salts of such metals as mercury, cadmium, zinc and magnesium. Detailed particulars as to such compounds and salts are disclosed in T. H. James, "The theory of the Photographic Process, pp 396–399" Macmillan.

The present compounds, even when allowed to coexist with other additives for light-sensitive silver halide photographic materials well patent to those skilled in the art, will not bring about any mutual interaction among them to mitigate their own effects. Such additives sinclude film hardners, chemical sensitizers, spectral ensitizers, surface active agents, and further pH regulators, thickening agents, antistatic agents, graininess improving agents, matting agents, etc.

In using the present compounds in silver halide color photographic materials, the compounds may be allowed to coexist with various constituents of said photographic materials well known to those skilled in the art, in addition to the above-mentioned various additives. Substances belonging to such constituents as referred to above include such compounds as forming dyes on reaction with an oxidized developing agent, i.e. the compounds are known as non-diffusible type couplers. More concretely, these couplers include yellow couplers represented by diketomethyl type compounds, magenta couplers represented by 5-pyrazolone type compounds, and cyan couplers represented by phenol type or naphthol type compounds, and furthers the so-called DIR couplers which release development inhibitors on color reaction and the so-called colored couplers which control masking density. These couplers mentioned above are exemplified in Research Disclosures (R.D.) 9232.

The present compounds are applicable to color photographic printing papers as light-sensitive silver halide color photographic materials. That is, generally various compounds are incorporated into silver halide emulsion layers or layers adjacent thereto for the purpose of imparting light fastness, resistance to humidity, thermal resistance, etc. to images obtained by the use of such couplers mentioned above. When the present compounds are allowed to coexist with the above-mentioned compounds, no mutual interaction among them to mitigate their own actions and effects. Such color image preservation improving agents include ultraviolet absorbers represented by benzotriazole type compounds and antioxidants represented by hydroquinone derivatives or phenol derivatives.

The present invention is illustrated below more concretely with reference to examples, but it should be construed that the content of the present invention is not limited to those examples.

EXAMPLE 1

A silver halide emulsion was prepared by subjecting a silver iodobromide emulsion prepared by the double jet process and containing 7 mol% of silver iodide to physical ripening, followed by desalting treatment. The silver halide thus prepared had an average particle diameter of 0.8 and more than 80% of the silver halide particles were found to be of the octahedron type. The content of silver halide in 1 kg of this emulsion was 1.2 moles. In a receptacle, 1 kg of this emulsion was charged with a gold sensitizer and sulfur sensitizer and then subjected to chemical ripening. After completion of the chemical ripening, the emulsion was charged with stirring with the under-mentioned sensitizing dye (150 mg/1 mole AgX) dissolved in methanol. The emulsion was divided into 7 portions, one of which was taken as a control, and the remaining 6 portions were individually incorporated with compounds as shown in Table 1. Each of the seven portions was successively incorporated with stirring with a 1% aqueous muco-chrolic acid solution (200 cc/1 mole AgX) and a 1% aqueous saponin solution (700 cc/1 mole AgX). Specimens of the emulsion thus prepared were individually coated on a cellulose triacetate base and then dried to ontain samples. Each sample thus obtained was suitable cut into sizes convenient for use in measurement, and then subjected to wedgwise exposure, development, stopping, fixing, water-washing and drying to obtain a strip having a black-and-white image thereon.

Sensitizing dye used:

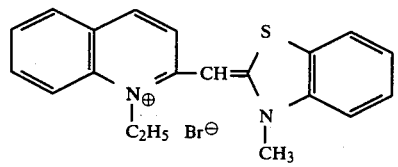

Exposure conditions employed: A light source having a color temperature of 5400° K. and a green filter (Wratten No. 58B manufactured by Eastman Kodak Co.) were used, and intensity of illumination employed was 64 luxed, 1/50 seconds.

Development conditions employed: Development of each exposed sample was developed at 27° C. for 3 minutes with a developer mentioned below.

Composition of developer:

| | |
|---|---|
| Monomethyl-p-aminophenol hydroquinone | 3 g |
| Hydroquinone | 6 g |
| Sodium carbonate (monohydrate) | 29.5 g |
| Anhydrous sodium sulfite | 50 g |
| Potassium bromide | 1 g |
| Water to make | 1 liter |

Each strip having the black-and-white image thereon was measured in green filter sensitivity ($S_G$) and fog by the use of KD type densitometer manufactured by Konishiroku Phot Industry Co., Ltd. to obtain the results as shown in Table 1 wherein $S_G$ of each sample was represented by a relative value as measured by assuming as 100 the value of $S_G$ of sample (1), i.e. the control.

TABLE 1

| Sample | Compound added (mg/1 mole AgX) | Fog | $S_G$ |
|---|---|---|---|
| (1) | Blank | 0.27 | 100 |
| (2) | 5-Mercapto-1-phenyltetrazole (100 mg) | 0.06 | 58 |
| (3) | 4-Hydroxy-6-methyl-1,3,3a,7-tetrazaindene (500 mg) | 0.17 | 92 |
| (4) | (3) + Present compound [I] −1 (20 mg) | 0.07 | 97 |
| (5) | Present compound [I] −1 (20 mg) | 0.08 | 95 |
| (6) | Present compound [I] −5 (20 mg) | 0.09 | 93 |
| (7) | Present compound [I] −1 (10 mg) + [I] −5 (10 mg) | 0.07 | 95 |

As can be seen from Table 1, the present compounds show favorable for inhibition properties without substantially lowering sensitivity, and even in the presence of other fog inhibiting compounds, the present compounds show synergistic action rather than lowering mutually their own actions and effects. Thud, the present compounds demonstrate that they have excellent fog inhibition effects.

EXAMPLE 2

A solution of 61 g of a yellow coupler, α-(1-benzyl-2,4-dioxy-3-imidazolydinyl)-α-pivaryl-2-chloro-5-γ-(2,4-di-t-amylphenoxy) butylamido acetanilide and 150 ml of 2,5-di-t-octylhydroquinone in 61 ml of dibutyl phthalate and 120 ml of ethyl acetate was incorporated into 500 ml of a 5% aqueous gelatin solution containing 3.0 g of sodium dodecylbenzenesulfonate. The mixture was dispersed by means of a homogenizer to prepare a dispersion. The dispersion thus obtained was incorporated into 1000 ml of a blue-sensitive silver chlorobromide (containing 10 mol% of silver chloride) emulsion containing the under-mentioned sensitizing dye. This emulsion was divided into seven portions, one of which portions was taken as a control, and the remaining six portions were individually incorporated with compounds as shown in Table 1. Each portion was successively chraged with stirring with a 5% methanol solution of triethylene phosponamide as a hardener (33 ml/1 mole AgX) and a 1% aqueous saponin solution (700 cc/1 mole AgX) to prepare a specimen of the emulsion. Specimens of the emulsion thus prepared were individually coated on a subbed cellulose triacetate base and then dried to prepare samples. Each of the samples thus prepared was suitably cut into sizes convenient for use in measurement, and then subjected to wedgewise exposure to blue light, color development, bleach-fixing, water-washing and drying to obtain a yellow image thereon.

Sensitizing dye used:

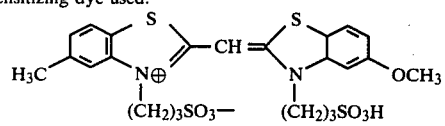

Processing step (32.8° C.)          Processing time

-continued

| | |
|---|---|
| Color development | 3' 30" and 7' |
| Bleach-fixing | 1' 30" |
| Water-washing | 3' 30" |
| Drying at 75–85° C. | |
| Composition of color developer: | |
| Benzyl alcohol | 16 ml |
| Ethylene glycol | 16 ml |
| Hydroxylamine sulfate | 3.0 g |
| 4-Amino-3-methyl-N-ethyl-N-($\beta$-methanesulfonamido) ethylaniline sulfate | 5.0 g |
| Potassium carbonate | 30 g |
| Potassium bromide | 0.6 g |
| Potassium chloride | 0.5 g |
| Potassium hydroxide | 2.5 g |
| Sodium polyphosphate | 1.0 g |
| Water to make 1 liter (pH 10.2) | |
| Composition of bleach-fixing solution: | |
| Ethylenediaminetetraacetic acid | 40 g |
| Ammonium sulfite (50% solution) | 30 g |
| Ammonium thiosulfate (70% solution) | 140 ml |
| Ammonia water (20% solution) | 30 ml |
| Iron (III) sodium ethylenediamine tetraacetate | 70 g |
| Water to make 1 liter (pH 7.10) | |

Each sample having the yellow image thereon was subjected to sensitometry by means of PDA-60 type sensitometer manufactured by Konishiroku Photo Industry Co., Ltd. to obtain the results as shown in Table 2, wherein sensitivities of each sample were represented by relative values as measured by assuming as 100 the sensitivities of sample (1) subjected to color development for 3 minutes and 30 seconds and 7 minutes, respectively.

TABLE 2

| Sample | Compound added (mg/1 mole AgX) | Development time 3' 30" Fog | Development time 3' 30" Sensitivity | Development time 7' Fog | Development time 7' Sensitivity |
|---|---|---|---|---|---|
| (1) | Blank | 0.10 | 100 | 0.19 | 100 |
| (2) | 5-Mercapto-1-phenyl-tetrazole (100 mg) | 0.06 | 60 | 0.07 | 63 |
| (3) | 4-Hydroxy-6-methyl-1,3,3a,7-tetrazaindene (500 mg) | 0.08 | 92 | 0.13 | 90 |
| (4) | (3) + Present compound [I] −1 (20 mg) | 0.06 | 98 | 0.07 | 97 |
| (5) | Present compound [I] −1 (20 mg) | 0.07 | 96 | 0.08 | 95 |
| (6) | Present compound [I] −5 (20 mg) | 0.06 | 98 | 0.08 | 95 |
| (7) | Present compound [I] −1 (10 mg) + [I] −5 (10 mg) | 0.06 | 98 | 0.07 | 96 |

As can be seen from Table 2, the present compounds show that only fog formation is effectively inhibited without substantially lowering sensitivity even when subjected to high temperature development treatment and also excessive development treatment. Furthermore, the present compounds demonstrate that even in the presence of other fog inhibiting compounds and other photographic additives, the present compounds do not mitigate their actions and effects and thus the present compounds possess excellent fog inhibition effects.

What we claim is:

1. A photographic material comprising a support and at least one silver halide emulsion layer coated thereon, which material comprises a compound represented by the following general formula [I]:

General formula [I]

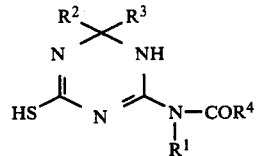

wherein $R^1$ represents a hydrogen atom or a substituted or unsubstituted aryl group, $R^2$ and $R^3$ individually represents a hydrogen atom, an alkyl group, alkenyl group, a substituted or unsubstituted aryl group, or $R^2$ and $R^3$ represent nonmetal atoms necessary for forming by their mutual linkage a 5- or 6-membered ring, and $R^4$ represents a hydrogen atom, an alkyl group, alkenyl group, a substituted or unsubstituted aryl group or a group of the general formula

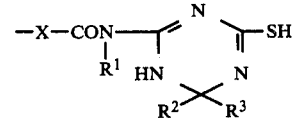

wherein X represents the group $-(CH_2)_n-$ (in which n represents a value of 0, 1, 2, 3, or 4) or an allylene group, and $R^1$, $R^2$ and $R^3$ are individually as defined above.

2. A photographic material according to claim 1, wherein $R^1$ in the general formula [I] represents hydrogen or lower alkyl.

3. A photographic material according to claim 2, wherein $R^1$ represents methyl or ethyl.

4. A photographic material according to claim 1, wherein $R^2$ and $R^3$ in the general formula [I] each represent lower alkyl group.

5. A photographic material according to claim 1 wherein $R^4$ in the general formula [I] represents alkyl having 1 to 18 carbon atoms.

6. A photographic material according to claim 5 wherein $R^4$ represents methyl or ethyl.

7. A photographic material according to claim 1, wherein the material comprises a dye forming coupler.

* * * * *